United States Patent
Kuechler et al.

(10) Patent No.: US 8,884,067 B2
(45) Date of Patent: Nov. 11, 2014

(54) PHENOL AND CYCLOHEXANONE MIXTURES

(75) Inventors: Keith H. Kuechler, Friendswood, TX (US); Francisco M. Benitez, Cypress, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 13/814,884

(22) PCT Filed: Aug. 16, 2011

(86) PCT No.: PCT/US2011/047837
§ 371 (c)(1), (2), (4) Date: May 13, 2013

(87) PCT Pub. No.: WO2012/036822
PCT Pub. Date: Mar. 22, 2012

(65) Prior Publication Data
US 2013/0225867 A1 Aug. 29, 2013

Related U.S. Application Data

(63) Continuation-in-part of application No. 13/143,975, filed as application No. PCT/US2010/021949 on Jan. 25, 2010, now Pat. No. 8,592,634.

(60) Provisional application No. 61/382,776, filed on Sep. 14, 2010, provisional application No. 61/155,746, filed on Feb. 26, 2009.

(51) Int. Cl.
| | | |
|---|---|---|
| *C07C 45/53* | (2006.01) | |
| *C07C 45/85* | (2006.01) | |
| *C07C 29/88* | (2006.01) | |
| *C07C 409/14* | (2006.01) | |
| *C07C 39/04* | (2006.01) | |
| *C07C 13/28* | (2006.01) | |
| *C07C 49/403* | (2006.01) | |

(52) U.S. Cl.
CPC ............... *C07C 45/85* (2013.01); *C07C 29/88* (2013.01); *C07C 409/14* (2013.01); *C07C 39/04* (2013.01); *C07C 13/28* (2013.01); *C07C 2101/14* (2013.01); *C07C 49/403* (2013.01)
USPC ............................ 568/376; 568/716; 568/798

(58) Field of Classification Search
USPC .......................................... 568/376, 716, 798
See application file for complete search history.

(56) References Cited

U.S. PATENT DOCUMENTS

| | | |
|---|---|---|
| 3,140,243 A | 7/1964 | Feder et al. |
| 3,140,318 A | 7/1964 | Sodomann et al. |
| 3,322,651 A | 5/1967 | Nielsen |
| 3,442,958 A | 5/1969 | Choo |
| 3,793,383 A | 2/1974 | Johnson et al. |
| 3,933,916 A | 1/1976 | Lejeune et al. |
| 4,021,490 A | 5/1977 | Hudson |
| 4,122,125 A | 10/1978 | Murtha et al. |
| 4,282,383 A | 8/1981 | Dai et al. |
| 4,328,372 A | 5/1982 | Wu |
| 5,064,507 A | 11/1991 | O'Donnell et al. |
| 6,037,513 A | 3/2000 | Chang et al. |
| 6,388,144 B1 | 5/2002 | Wijesekera et al. |
| 7,002,048 B2 | 2/2006 | Wijesekera et al. |
| 7,205,442 B2 | 4/2007 | Payne |
| 7,579,511 B1 | 8/2009 | Dakka et al. |
| 2003/0163007 A1 | 8/2003 | Dyckman et al. |
| 2006/0211890 A1 | 9/2006 | Fodor |
| 2007/0032681 A1 | 2/2007 | Walsdorff et al. |
| 2011/0105805 A1 | 5/2011 | Buchanan et al. |
| 2011/0301387 A1 | 12/2011 | Wang et al. |

FOREIGN PATENT DOCUMENTS

WO    WO2010/098916 A2 *  9/2010

OTHER PUBLICATIONS

Schmidt, Robert J., "*Industrial Catalytic Processes—Phenol Production*," Applied Catalysis A: General, 2005, vol. 280, pp. 89-103.

* cited by examiner

*Primary Examiner* — Sikarl Witherspoon
(74) *Attorney, Agent, or Firm* — Jamie L. Sullivan; Siwen Chen (57) ABSTRACT

In a process for producing phenol and cyclohexanone, a feed comprising cyclohexylbenzene is oxidized to produce an oxidation reaction product comprising cyclohexyl-1-phenyl-1-hydroperoxide. At least a portion of the oxidation reaction product is then cleaved to produce a cleavage reaction product comprising phenol, cyclohexanone, and at least one contaminant. At least a portion of the cleavage reaction product is contacted with an acidic material to convert at least a portion of the at least one contaminant to a converted contaminant and thereby produce a modified reaction product. The cleavage reaction product may comprise 1 wt %-30 wt % phenol; 1 wt %-30 wt % cyclohexanone; and 0.1 wt % to 10 wt % of at least one of water, bicyclohexane, cyclohexenylbenzene, methylcyclopentanone, 1-phenylhexan-1-one, cyclohexyldione, cyclohexanol, cyclohexenone, hydroxycyclohexanone, benzoic acid, phenyl cyclohexanol, hexanal and 1-phenyl-6-hydroxyhexan-1-one, wherein the wt %s are based upon the total weight of the mixture.

23 Claims, 2 Drawing Sheets

PHENOL AND CYCLOHEXANONE MIXTURES

PRIORITY CLAIM

This application is a National Stage Application of International Application No. PCT/US2011/047837 filed Aug. 16, 2011, which claims priority to and the benefit of U.S. Provisional Application Ser. No. 61/382,776 filed on Sep. 14, 2010, which are hereby incorporated by reference in their entirety. This application also claims priority to and the benefit of, and is a continuation-in-part of, U.S. patent application Ser. No. 13/143,975, filed on Jan. 25, 2010, now granted U.S. Pat. No. 8,592,634, granted Nov. 26, 2013 and entitled "Process for Producing Phenol", which, in turn, is a national stage application of International Application No. PCT/US2010/021949, which, in turn, claims priority to U.S. Provisional Application Ser. No. 61/155,746, the contents of all of which are incorporated herein by reference in their entirety.

FIELD

The present invention relates to phenol and cyclohexanone mixtures.

BACKGROUND

Phenol is most commonly produced by the Hock process. The Hock process involves alkylation of benzene with propylene to produce cumene, oxidation of the cumene to the corresponding hydroperoxide, and cleavage of the hydroperoxide to produce equimolar amounts of phenol and acetone.

The various steps involved in the production of phenol and acetone from cumene can produce various contaminants that are difficult to separate from the desired phenol and acetone. These contaminants, if left in the phenol product, may cause difficulties in downstream processing, or render the phenol unusable for such downstream processing, for example in the subsequent production of bis-phenols and polycarbonates. Therefore, techniques have been proposed to remove those contaminants involving certain treatments. For example, U.S. Pat. No. 5,064,507 discloses obtaining high purity phenol from cleavage of cumene hydroperoxide through one or more amine treatment steps. The phenol mixture includes at least 0.5 wt % to no greater than 10 wt % of alpha-methylstyrene, and further includes acetol, 2-phenyl-propionaldehyde (2PPA), methyl-benzofuran (MBF), mesityl oxide (MO) and carbonyl impurities. In addition, U.S. Pat. No. 3,322,651 discloses a method of producing phenol made by decomposition of cumene hydroperoxide. The phenol is purified by contacting the carbonyl compounds with a nitrogen compound.

Cyclohexanone is typically produced by the oxidation of cyclohexane, or the hydrogenation of phenol. These methods can also generate various contaminants that are difficult to separate from the desired product, and that can render the cyclohexanone product substandard or unusable to downstream processes, for example in the manufacture of caprolactam or adipic acid, or further using those derivatives in the production of one or another type of nylon. Thus, certain treatment means have been described to remove those contaminants from cyclohexanone. For example, U.S. Pat. No. 7,199,271 discloses a method for reducing the concentration of cyclohexenone in a cyclohexanone-containing organic mixture. The method includes contacting an organic mixture comprising cyclohexenone with an effective amount of at least one of sulfurous acid, a salt of sulfurous acid, an alkali hydroxide, or a mixture of two or more of these compounds.

The production of phenol from cyclohexylbenzene is an emerging technology, interesting in that it co-produces cyclohexanone rather than acetone. Cyclohexylbenzene can be produced, for example, by direct alkylation of benzene with cyclohexene, or as disclosed in U.S. Pat. No. 6,037,513, by contacting benzene with hydrogen in the presence of a catalyst. The cyclohexylbenzene can then be oxidized to the corresponding hydroperoxide and the peroxide cleaved to phenol and cyclohexanone using an acidic cleavage catalyst.

The production of phenol and cyclohexanone from cyclohexylbenzene also produces various contaminants that are difficult to separate from the desired products. However, the nature of those contaminants and the separations involved are significantly different than those involved in either the conventional Hock process for phenol and acetone, or the conventional production of cyclohexanone from cyclohexane or phenol. For example, hydroalkylation of benzene produces significant amounts of, inter alia, cyclohexane and lesser amounts of methylcyclopentane, cyclohexene, phenylcyclohexene, and phenylcyclohexyldiene. Similarly, the oxidation of cyclohexylbenzene typically produces peroxide species alien to the Hock process, such as the desired cyclohexyl-1-phenyl-1-hydroperoxide (CHBHP), and undesired byproduct hydroperoxides such as cyclohexyl-1-phenyl-2-hydroperoxide, cyclohexyl-1-phenyl-3-hydroperoxide and cyclohexyl-1-phenyl-4-hydroperoxide. Finally, the cleavage of these various hydroperoxides produces, as both the product of the undesired hydroperoxides and the undesired byproducts of the desired CHBHP, a wide variety of contaminant species are not produced by the chemistry and technology of either the Hock process, or the cyclohexane oxidation or phenol hydrogenation processes.

Methods are needed to manage the contaminants generated when manufacturing phenol and cyclohexanone from cyclohexylbenzene, and enable the manufacture of high quality phenol or cyclohexanone products.

Moreover, such contaminants can be particularly difficult to separate in continuous processes, and it can become increasingly more costly to separate the contaminants in the later stages (e.g., due to similarity in boiling points, etc.). As such, it would be advantageous to form compositions in the intermediate stages of the process (e.g., the compositions formed post-hydroalkylation, post-oxidation, post-cleavage and post-neutralization) that contain a reduced or minimized level of contaminants.

SUMMARY

In various embodiments, the invention relates to a mixture comprising:
(a) 1 wt %-30 wt % phenol;
(b) 1 wt %-30 wt % cyclohexanone; and
(c) 0.1 wt %-10 wt % of at least one of water, bicyclohexane, cyclohexenylbenzene, methylcyclopentanone, 1-phenylhexan-1-one, cyclohexyldione, cyclohexanol, cyclohexenone, hydroxycyclohexanone, benzoic acid, phenyl cyclohexanol, hexanal and 1-phenyl-6-hydroxyhexan-1-one, wherein the wt %s are based upon the total weight of the mixture.

A mixture comprising:
(a) 1 wt %-30 wt % phenol;
(b) 1 wt %-30 wt % cyclohexanone; and
(c) 0.1 wt %-10 wt % of at least one of:
 (1) 100 wppm to 3.0 wt % of water;

(2) 10 wppm to 3.0 wt % of at least one of bicyclohexane and cyclohexenylbenzene;
(3) 10 wppm to 4.0 wt % of at least one of methylcyclopentanone and 1-phenylhexan-1-one;
(4) 10 wppm to 1.0 wt % of cyclohexyldione;
(5) 10 wppm to 1.0 wt % of cyclohexanol;
(6) 10 wppm to 2.0 wt % of cyclohexenone;
(7) 10 wppm to 2.0 wt % of hydroxycyclohexanone;
(8) 10 wppm to 1.0 wt % of benzoic acid;
(9) 10 wppm to 5.0 wt % of phenyl cyclohexanol;
(10) 10 wppm to 1.0 wt % of hexanal; and
(11) 10 wppm to 4.0 wt % of 1-phenyl-6-hydroxyhexan-1-one,
wherein the wppms and wt % s are based upon the total weight of the mixture.

DETAILED DESCRIPTION OF THE EMBODIMENTS

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention can be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

The present invention is directed to a process for producing phenol and cyclohexanone from cyclohexylbenzene and, more particularly, to an integrated process for producing phenol and cyclohexanone from benzene via cyclohexylbenzene as an intermediate. In the process the cyclohexylbenzene is initially oxidized to produce an oxidation reaction product comprising cyclohexyl-1-phenyl-1-hydroperoxide and at least a portion of the oxidation reaction product is cleaved to produce a cleavage reaction product comprising phenol, cyclohexanone, and one or more contaminants. Often some or all of the contaminants in the cleavage reaction product are difficult to separate from the phenol and/or cyclohexanone by simple methods, such as distillation. Thus, in the present process, at least a portion of the cleavage reaction product is contacted with an acidic material under conditions to convert at least one of the contaminants to a converted contaminant, which is more readily separable from the phenol and/or cyclohexanone.

Production of the Cyclohexylbenzene

In the integrated process for producing phenol and cyclohexanone from benzene, the benzene is initially converted to cyclohexylbenzene by any conventional technique, including alkylation of benzene with cyclohexene in the presence of an acid catalyst, such as zeolite beta or an MCM-22 family molecular sieve, or by oxidative coupling of benzene to make biphenyl followed by hydrogenation of the biphenyl. However, in practice, the cyclohexylbenzene is generally produced by contacting the benzene with hydrogen under hydroalkylation conditions in the presence of a hydroalkylation catalyst whereby the benzene undergoes the following reaction (1) to produce cyclohexylbenzene (CHB):

For an example of hydroalkylation of benzene in the presence of hydrogen for the production of cyclohexylbenzene, see U.S. Pat. Nos. 6,730,625 and 7,579,511 which are incorporated by reference. Also, see International Applications WO2009131769 or WO2009128984 directed to catalytic hydroalkylation of benzene in the presence of hydrogen for the production of cyclohexylbenzene.

Any commercially available benzene feed can be used in the hydroalkylation reaction, but preferably the benzene has a purity level of at least 99 wt %. Similarly, although the source of hydrogen is not critical, it is generally desirable that the hydrogen is at least 99 wt % pure.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa. Suitable values for the molar ratio of hydrogen to benzene are between about 0.15:1 and about 15:1, such as between about 0.4:1 and about 4:1 for example between about 0.4 and about 0.9:1.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes molecular sieves having the MWW framework topology. (Such crystal structures are discussed in the "Atlas of Zeolite Framework Types", Fifth edition, 2001, the entire content of which is incorporated as reference).

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 wt % and about 10 wt %, such as between about 0.1 wt % and about 5 wt %, of the catalyst.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia.

Although the hydroalkylation reaction is highly selective towards cyclohexylbenzene, the effluent from the hydroalkylation reaction may contain some dialkylated products, as well as unreacted benzene and the desired monoalkylated species. The unreacted benzene may be recovered by distillation and recycled to the alkylation reactor. The bottoms from the benzene distillation are further distilled to separate the monocyclohexylbenzene product from any dicyclohexylbenzene and other heavies. Depending on the amount of dicyclohexylbenzene present in the reaction effluent, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, zeolite USY, and mordenite. The transalkylation reaction is typically conducted under at least partial liquid phase conditions, which suitably include a temperature of about 100° C. to about 300° C., a pressure of about 800 kPa to about 3500 kPa, a weight hourly space velocity of about 1 to about 10 hr$^{-1}$ on total feed, and a benzene/dicyclohexylbenzene weight ratio about of 1:1 to about 5:1.

After removal of the unreacted benzene and the polyalkylated benzenes and other heavy species, the cyclohexylbenzene is fed to the oxidation reaction. Typically, however, this cyclohexylbenzene feed contains the following contaminants generated as by-products of its synthesis:

between 1 wppm and 1 wt % bicyclohexane, or between 10 wppm and 8000 wppm bicyclohexane;
between 1 wppm and 1 wt % biphenyl, or between 10 wppm and 8000 wppm biphenyl;
between 1 wppm and 2 wt % methylcyclopentylbenzene, or between 10 wppm and 1 w % methylcyclopentylbenzene as any isomer: 1-phenyl-1-methylcyclopentane, 1-phenyl-2-methylcyclopentane, and 1-phenyl-3-methylcyclopentane; and
less than about 1000 wppm, such as less than 100 wppm of phenol, olefins or alkylene benzenes, such as cyclohexenyl benzene.

Oxidation Reaction

As discussed above, the process includes oxidizing at least a portion of a feed comprising cyclohexylbenzene to produce an oxidation composition comprising cyclohexyl-1-phenyl-1-hydroperoxide. As used herein, "oxidizing" means causing an oxidation reaction to occur.

The feed comprising cyclohexylbenzene may be produced by any process known to those in the art, and in accordance with this invention may contain a small amount of certain byproduct components that are difficult to remove from cyclohexylbenzene, discussed later. The hydroalkylation process may generate byproduct dicyclohexylbenzene, and thus be accompanied by and integrated with the transalkylation of byproduct dicyclohexylbenzene with benzene to produce additional cyclohexylbenzene, and may further include various separations to recover and recycle unreacted benzene, and remove heavy alkylates and other unselective byproducts. Another known method to manufacture a feed comprising cyclohexylbenzene involves the catalytic alkylation of benzene with cyclohexene.

Further, in an embodiment, a portion of the feed comprising cyclohexylbenzene may be a recycle stream comprising cyclohexylbenzene produced by the processing of the treated cleavage reaction mixture, discussed later. In this manner, all or a fraction of cyclohexylbenzene that was unreacted in the oxidation reaction may be recovered and reused to generate additional phenol.

Regardless of the source or sources, in various embodiments, a feed comprising cyclohexylbenzene contains at least about 10 wt %, or at least about 25 wt %, or at least about 50 wt %, or at least about 65 wt %, or at least about 75 wt %, or at least about 95 wt %, or at least about 99 wt % cyclohexylbenzene. In various embodiments, it may contain another component. For example, the feed comprising cyclohexylbenzene may contain at least 1 wppm and no greater than 1 wt % bicyclohexane, or at least 10 wppm and no greater than 8000 wppm bicyclohexane. It may contain at least 1 wppm and no greater than 1 wt % biphenyl, or at least 10 wppm and no greater than 8000 wppm biphenyl. It may contain at least 1 wppm and no greater than 2 wt % methylcyclopentylbenzene, or at least 10 wppm and no greater than 1 w % methylcyclopentylbenzene as any isomer: 1-phenyl-1-methylcyclopentane, 1-phenyl-2-methylcyclopentane, and 1-phenyl-3-methylcyclopentane. There may be other components present, though desirably of low concentration, say, no greater than 1000 wppm, or no greater than 100 wppm of phenol, olefins or alkylene benzenes such as cyclohexenyl benzene, individually or in any combination. The feed comprising cyclohexylbenzene to which oxygen is introduced to cause an oxidation reaction may contain cyclohexylbenzene, any other one component, or any combination of the other components just noted in the proportions for each or in combination just noted.

In various exemplary embodiments, oxidation may be accomplished by contacting an oxygen-containing gas, such as air and various derivatives of air, with the feed comprising cyclohexylbenzene. For example, one may use air that has been compressed and filtered to removed particulates, air that has been compressed and cooled to condense and remove water, or air that has been enriched in oxygen above the natural approximately 21 mol % in air through membrane enrichment of air, cryogenic separation of air or other means within the ken of the skilled artisan.

The oxidation may be conducted in the absence or presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 wt % to 15 wt %, such as between 0.001 wt % to 5 wt %, of the cyclohexylbenzene.

In various embodiments, the oxidation reaction occurs under oxidation conditions. Suitable oxidation conditions include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

Typically, the product of the oxidation of a feed comprising cyclohexylbenzene, i.e., the oxidation composition, contains at least 5 wt %, such as at least 10 wt %, for example at least 15 wt %, or at least 20 wt % cyclohexyl-1-phenyl-1-hydroperoxide based upon the total weight of the oxidation composition. In other manifestations, the oxidation composition contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation composition. The oxidation composition may further comprise imide catalyst and unreacted cyclohexylbenzene. The invention may include cyclohexylbenzene in the oxidation composition in an amount of at least 50 wt %, or at least 60 wt %, or at least 65 wt %, or at least 70 wt %, or at least 80 wt %, or at least 90 wt %, based upon total weight of the oxidation composition.

In addition, the oxidation composition may contain one or more hydroperoxides other than cyclohexyl-1-phenyl-1-hydroperoxide generated as a byproduct of the oxidation reaction of cyclohexylbenzene, or as the oxidation product of some oxidizable component other than cyclohexylbenzene that may have been contained in the cyclohexylbenzene undergoing oxidation. Such oxidizable contaminants include methylcyclopentylbenzenes of various isomers, and bicyclohexane. Other exemplary hydroperoxide contaminants present in the oxidation composition include at least, based on the total weight of the oxidation composition, 0.1 wt % to no greater than 10 wt %, or at least 0.5 wt % to no greater than 5.0 wt %, or at least 1 wt % and no greater than 4 wt % of any one or any combination of: cyclohexyl-1-phenyl-2-hydroperoxide, cyclohexyl-1-phenyl-3-hydroperoxide, cyclohexyl-1-phenyl-4-hydroperoxide; cyclopentyl-1-methyl-2-phenyl-2-hydroperoxide, cyclopentyl-1-methyl-3-phenyl-3-hydroperoxide, cyclopentyl-1-methyl-1-phenyl-2-hydroperoxide, cyclopentyl-1-methyl-1-phenyl-3-hydroperoxide; and cyclohexyl-1-phenyl-1,2-dihydroperoxide, cyclohexyl-1-phenyl-1,3-dihydroperoxide, cyclohexyl-1-phenyl-1,4-dihydroperoxide; cyclopentyl-1-methyl-2-phenyl-1,2-dihydroperoxide, cyclopentyl-1-methyl-2-phenyl-2,3-dihydroperoxide, cyclopentyl-1-methyl-2-phenyl-2,4-dihydroperoxide, and cyclopentyl-1-methyl-2-phenyl-2,5-dihydroperoxide.

The reactor used for the oxidation of cyclohexylbenzene, i.e., the oxidation reactor, may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel container with a distributor inlet for the oxygen-containing stream in line. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner well known to those skilled in the art.

At least a portion of the oxidation composition may be subjected to a cleavage reaction, which may include all or some fraction of the oxidation composition as directly produced without undergoing any separation (e.g., some fraction resulting from diverting some amount of the oxidation composition as directly produced to another disposition, such as temporary storage). Thus, the at least a portion of the oxidation composition may have the same composition as the oxidation composition. Further, all or some of the oxidation composition as directly produced may undergo one or more separations, and an appropriate product of that separation (or separations), now modified in composition relative the oxidation composition as directly produced, may provide the at least a portion of the oxidation composition subjected to the cleavage reaction.

For example, all or a fraction of the oxidation composition as directly produced may be subjected to high vacuum distillation, to generate a product enriched in unreacted cyclohexylbenzene relative to the oxidation composition, and the at least a portion of the oxidation composition as a residue concentrated in the desired cyclohexyl-1-phenyl-1-hydroperoxide that may be subjected to a cleavage reaction. Cyclohexylbenzene is essentially a diluent in the cleavage reaction and the neutralization reaction, and further is not a good solvent for most acid catalysts, particularly sulfuric acid. However, distinctive from the Hock process described earlier, it is convenient in the present invention that the at least a portion of the oxidation composition that will undergo the cleavage reaction be of the same composition of cyclohexylbenzene as the oxidation composition directly produced. That is to say, it is convenient that the at least a portion of the oxidation composition undergo no concentration of the hydroperoxide(s) before the acid catalyst is introduced to it, because the starting alkylbenzene cyclohexylbenzene has a significantly higher normal boiling point than the starting alkylbenzene cumene that is found in the Hock process. While within the scope of the present invention, any practical separation attempted to concentrate the cyclohexyl-1-phenyl-1-hydroperoxide or other hydroperoxides from cyclohexylbenzene prior to effecting the cleavage reaction likely requires inconvenient very low vacuum pressure distillation equipment, and even then likely requires very high temperatures that could cause dangerous, uncontrolled thermal decomposition of the hydroperoxides.

Additionally or alternatively, all or a fraction of the oxidation composition, or all or a fraction of the vacuum distillation residue may be cooled to cause crystallization of the unreacted imide oxidation catalyst, which can then be separated either by filtration or by scraping from a heat exchanger surface used to effect the crystallization, and provide an at least a portion of the oxidation composition reduced or free from imide oxidation catalyst that may be subjected to a cleavage reaction.

As another example, all or a fraction of the oxidation composition as produced may be subjected to water washing and then passage through an adsorbent, such as a 3 A molecular sieve, to separate water and other adsorbable compounds, and provide an at least a portion of the oxidation composition with reduced water or imide content that may be subjected to a cleavage reaction. Similarly, all or a fraction of the oxidation composition may undergo a chemically or physically based adsorption, such as passage over a bed of sodium carbonate to remove the imide oxidation catalyst (e.g., NHPI) or other adsorbable components, and provide an at least a portion of the oxidation composition reduced in oxidation catalyst or other adsorbable component content that may be subjected to a cleavage reaction. Another possible separation involves contacting all or a fraction of the oxidation composition as produced with a liquid containing a base, such as an aqueous solution of an alkali metal carbonate or hydrogen carbonate, to form an aqueous phase comprising a salt of the imide oxidation catalyst, and an organic phase reduced in imide oxidation catalyst provided as an at least a portion of the oxidation composition that may be subjected to a cleavage reaction.

Cleavage Reaction

As discussed above, the process includes cleaving at least a portion of the oxidation composition in the presence of an acid catalyst to produce a cleavage reaction mixture comprising the acid catalyst, phenol, and cyclohexanone. As used herein, "cleaving" means causing a cleavage reaction to occur. In the cleavage reaction, at least a portion of the desired cyclohexyl-1-phenyl-1-hydroperoxide will decompose in high selectivity to cyclohexanone and phenol, and further, any other hydroperoxides present will decompose to various products, discussed below.

In various embodiments, the acid catalyst is at least partially soluble in the cleavage reaction mixture, stable at a temperature of at least 185° C. and has a lower volatility (higher normal boiling point) than cyclohexylbenzene. In various embodiments, the acid catalyst is also at least partially soluble in the treated cleavage reaction mixture.

Acid catalysts include, but are not limited to, Bronsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage reaction mixture contains at least 50 weight-parts-per-million (wppm) and no greater than 3000 wppm of the acid catalyst, or at least 150 wppm to and no greater than 2000 wppm of the acid catalyst, or at least 300 wppm and no greater than 1500 wppm of the acid catalyst, based upon total weight of the cleavage reaction mixture.

In various embodiments of the present invention, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

As a result of potentially high amounts of cyclohexylbenzene in the cleavage reaction mixture, considerably higher than cumene in the Hock process material undergoing a cleavage reaction, it may be convenient in the present invention to use more acid catalyst to effect the cleavage reaction than typically believed optimal in the Hock process, to at least partially overcome the insolubility of the acid in the cleavage reaction mixture. However, lower amounts of acid catalyst may be applied in the present invention, with appropriate additional cleavage reactor volume and residence time of the cleavage reaction mixture in the cleavage reactor to obtain high hydroperoxide conversion.

In various embodiments, the cleavage reaction occurs under cleavage conditions. Suitable cleavage conditions include a temperature of at least 20° C. and no greater than 200° C., or at least 40° C. and no greater than 120° C., and a pressure of at least 1 and no greater than 370 psig (at least 7 kPa, gauge and no greater than 2,550 kPa, gauge), or at least 14.5 psig and no greater than 145 psig (at least 100 kPa, gauge and no greater than 1,000 kPa, gauge) such that the cleavage reaction mixture is completely or predominantly in the liquid phase during the cleavage reaction.

Conversion of any hydroperoxide, such as cyclohexyl-1-phenyl-1-hydroperoxide, and conveniently all cyclohexyl-1-phenyl-1-hydroperoxide and other hydroperoxides, is generally very high in the cleavage reaction, e.g., at least 90.0 wt %, or at least 95.0 wt %, or at least 98.0 wt %, or at least 99.0 wt %, or at least 99.5 wt %, or at least 99.9 wt %, or even 100 wt %, the percentage conversion based on the weight of a given specie of hydroperoxide, or of all cyclohexyl-1-phenyl-1-hydroperoxide and other hydroperoxides present in the at least a portion of the oxidation composition undergoing the cleavage reaction. This is desirable because any hydroperoxide, even the cyclohexyl-1-phenyl-1-hydroperoxide, becomes a contaminant in the cleavage reaction mixture and treated cleavage reaction mixture, discussed below. Hydroperoxides cause undesired chemistry when decomposed under uncontrolled conditions outside the cleavage reaction, or if thermally decomposed under the conditions in a distillation column.

The major products of the cleavage reaction of cyclohexyl-1-phenyl-1-hydroperoxide are phenol and cyclohexanone, each of which generally comprise about 40 wt % to about 60 wt %, or about 45 wt % to about 55 wt % of the cleavage reaction mixture, such wt % based on the weight of the cleavage reaction mixture exclusive of unreacted cyclohexylbenzene and acid catalyst.

The cleavage reaction mixture may comprise no greater than 30 wt %, or no greater than 25 wt %, or no greater than about 15 wt % of phenol, or it may comprise at least 1 wt %, or at least 3 wt %, or at least 5 wt %, or at least 10 wt % phenol, based on total weight of the cleavage reaction mixture. Further, the cleavage reaction mixture may comprise no greater than 30 wt %, or no greater than 25 wt %, or no greater than about 15 wt % of cyclohexanone, or it may comprise at least 1 wt %, or at least 3 wt %, or at least 5 wt %, or at least 10 wt % cyclohexanone, based on total weight of the cleavage reaction mixture.

The cleavage reaction mixture may further comprise at least 0.1 wt % and no greater than 10 wt %, or at least 0.5 wt % and no greater than 7 wt %, or at least 1 wt % and no greater than 5 wt %, or at least 1.5 and no greater than 3 wt % of any one or combination of contaminant byproducts based on the total weight of the cleavage reaction mixture.

As used herein, a "contaminant" or a "contaminant byproduct" may include any unwanted hydrocarbon or oxygenated hydrocarbon component in the cleavage reaction mixture or the neutralized cleavage mixture, or any portion of either; that is anything other than phenol, cyclohexanone, and cyclohexylbenzene. They are unwanted because their presence indicates a decreased yield of desired product phenol and cyclohexanone from cyclohexylbenzene, or they cause difficulties in the separation and purification of phenol, cyclohexanone or unconverted cyclohexylbenzene, or some combination thereof. A contaminant in the cleavage reaction mixture or the neutralized cleavage mixture or any portion thereof may have been produced in any element of the present invention, or may have been contained in the feed comprising cyclohexylbenzene undergoing oxidation. For example, a contaminant may be present in the cleavage reaction mixture as a result of one or more of: (i) it was included with the cyclohexylbenzene (e.g., as a byproduct of production using hydroalkylation or alkylation); (ii) it was produced in oxidation of the feed comprising cyclohexylbenzene, and potentially the oxidation of an oxidizable component from (i); and/or (iii) it was produced in the cleavage reaction of at least a portion of the oxidation composition from (ii).

Examples of contaminants in the cleavage reaction mixture, and possible amounts thereof, include (weight-parts-per-million (wppm) and wt % are based upon total weight of the cleavage reaction mixture):

water, e.g., at least 100 wppm and no greater than 3.0 wt %;

twelve carbon, two ringed hydrocarbons other than cyclohexylbenzene, such as bicyclohexane, cyclohexenylcyclohexane, and cyclohexadienylcyclohexane, cyclohexenylbenzene, cyclohexadienylbenzene and biphenyl, e.g., at least 10 wppm and no greater than 3.0 wt %, each or in total;

saturated and unsaturated ketones, such as pentanones, methylcyclopentanones, hexanones, 1-phenylhexan-1-one and 1-cyclohexylhexan-1-one, phenylcyclohexanones and phenylmethylcyclopentanones, e.g., at least 10 wppm and no greater than 4.0 wt %, each or in total;

cyclohexyldione(s), e.g., at least 10 wppm and no greater than 1.0 wt % in total;

less than 12 carbon, unsaturated hydrocarbons, cyclic and acyclic, or combinations thereof, such as cyclohexene, e.g., at least 10 wppm and no greater than 1.0 wt %, each or in total;

cyclohexanol, e.g., at least 10 wppm and no greater than 1.0 wt %;

cyclohexenone(s), e.g., 2-cyclohexenone or 3-cyclohexenone, e.g., at least 10 wppm and no greater than 2.0 wt %, each or in total;

hydroxycyclohexanone(s), e.g., at least 10 wppm and no greater than 2.0 wt % in total;

carboxylic acids, such as benzoic acid, e.g., at least 10 wppm and no greater than 1.0 wt %, each or in total;

phenyl cyclohexanol(s), e.g., 1-phenylcyclohexan-1-ol, 2-phenylcyclohexan-1-ol, 3-phenylcyclohexan-1-ol and 4-phenylcyclohexan-1-ol, e.g., at least about 10 wppm and no greater than 5.0 wt %, each or in total;

cyclohexyl cyclohexanol(s), such as 1-cyclohexylcyclohexan-1-ol, 2-cyclohexylcyclohexan-1-ol, 3-cyclohexylcyclohexan-1-ol, and 4-cyclohexylcyclohexan-1-ol, e.g., at least 10 wppm and no greater than 1.0 wt %, each or in total;

unsaturated alkyl oxygenated cyclohexanes, such as cyclohexenyl cyclohexanols and cyclohexenyl cyclohexanones, and methylcyclopentenyl cyclohexanols and methylcyclopentenyl cyclohexanones, e.g., at least 10 wppm and no greater than 1.0 wt %, each or in total;

aldehydes, especially, pentanals, hexanals, cyclohexyl or methylcyclopentyl alkyl aldehydes, such 5-cyclohexyl hexanal, and 6-hydroxy-5-cyclohexyl hexanal, e.g., at least 10 wppm and no greater than 1.0 wt %, each or in total;

1-phenyl-6-hydroxyhexan-1-one (also called 6-hydroxyhexanophenone), e.g., at least 10 wppm and no greater than 4.0 wt %;

1-cyclohexyl-6-hydroxyhexan-1-one, e.g., at least 10 wppm and no greater than 1.0 wt %;

benzoic esters, e.g., at least 10 wppm and no greater than 1.0 wt %, each or in total; and a hydroperoxide (e.g., an unreacted hydroperoxide). Non-limiting examples include: the desired cyclohexyl-1-phenyl-1-hydroperoxide, and the other hydroperoxides such as cyclohexyl-1-phenyl-2-hydroperoxide, cyclohexyl-1-phenyl-3-hydroperoxide, cyclohexyl-1-phenyl-4-hydroperoxide; cyclopentyl-1-methyl-2-phenyl-2-hydroperoxide, cyclopentyl-1-methyl-3-phenyl-3-hydroperoxide, cyclopentyl-1-methyl-1-phenyl-2-hydroperoxide, cyclopentyl-1-methyl-1-phenyl-3-hydroperoxide, cyclohexyl-1-phenyl-1,2-dihydroperoxide, cyclohexyl-1-phenyl-1,3-dihydroperoxide, cyclohexyl-1-phenyl-1,4-dihydroperoxide; cyclopentyl-1-methyl-2-phenyl-1,2-dihydroperoxidep, cyclopentyl-1-methyl-2-phenyl-2,3-dihydroperoxide, cyclopentyl-1-methyl-2-phenyl-2,4-dihydroperoxide, and cyclopentyl-1-methyl-2-phenyl-2,5-dihydroperoxide; e.g., at least 1 wppm and no greater than 1.0 wt %, each or in total.

The reactor used to effect the cleavage reaction (i.e., the cleavage reactor) may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

At least a portion of the cleavage reaction mixture may be subjected to a neutralization reaction, which may include all or some fraction of the cleavage reaction mixture as directly produced without undergoing any separation (e.g., some fraction resulting from diverting some amount of the cleavage reaction mixture as directly produced to another disposition, such as temporary storage). Thus, the at least a portion of the cleavage reaction mixture may have the same composition as the cleavage reaction mixture. Further, all or some of the cleavage reaction mixture as directly produced may undergo one or more separations, and an appropriate product of that separation (or separations), now modified in composition relative the cleavage reaction mixture as directly produced, may provide the at least a portion of the cleavage reaction mixture subjected to the neutralization reaction.

Contaminant Treatment

As discussed above, the cleavage reaction mixture may comprise one or more contaminants. In various embodiments disclosed herein, the processes further comprise contacting at least a portion of a contaminant with an acidic material to convert at least a portion of the contaminant to a converted contaminant, thereby producing a modified reaction mixture.

Suitable acidic material for use in treating the cleavage reaction product include microporous acidic materials, such as zeolites, aluminas and aluminosilicates, especially zeolites having a pore diameter over 4 Angstrom; cation exchange resins, especially sulfonic resins, such as Rohm & Haas Amberlyst 16; Bronsted acids, such as formic acid acetic acid, hydrochloric acid and sulfuric acid; sulfurous acid or salts thereof, such as sodium sulfate, sodium hydrogen bisulfate and sodium metabisulfite; and aqueous acid solutions. In one embodiment, the acidic material used to treat the cleavage reaction product comprises at least part of the acid catalyst used to promote the cleavage reaction.

Conveniently, the acidic material has a relatively low volatility, with a normal boiling point above phenol and/or cyclohexylbenzene, such that it will tend to distill in the bottoms product in subsequent fractionation operations that may be conducted.

The contaminant treatment can be conducted directly on the cleavage reaction mixture, or after one or more separations of the cleavage reaction mixture. For example, the cleavage reaction mixture may be separated (e.g., by distillation) into phenol-rich and cyclohexanone-rich fractions before or after the contaminants are subjected to contaminant treatment.

Suitable contaminant treatment conditions vary with the acidic material employed. Treatment conditions include a temperature of at least about 30° C., or at least about 35° C., or at least about 40° C., or at least about 50° C., or at least about 60° C., or at least about 70° C., or at least about 80° C., or at least about 90° C., or at least about 100° C. In various embodiments, the temperature is less than about 250° C., or less than about 225° C., or less than about 190° C., or less than about 180° C., or less than about 170° C., or less than about 160° C., or less than about 150° C., or less than about 140° C. The temperature may be any range of the aforementioned temperatures.

The pressure may be about 0.75 psig to about 500 psig (5 kPa to 3450 kPa), or about 10 psig to 200 psig (70 kPa to 1380 kPa) such that the cleavage reaction mixture is completely or predominantly in the liquid phase during the treatment.

In various embodiments, the pressure may be about 10 psig to 200 psig (170 kPa to 1380 kPa) and the temperature may be about 60° C. to about 160° C., such that most of the cleavage reaction mixture is in the liquid phase.

In embodiments in which the acidic material is a solid microporous material (e.g., zeolites, aluminas, etc.), the pressure may be about 10 psig to 200 psig (70 kPa to 1380 kPa) and the temperature may be about 100° C. to about 250° C., such that most of the cleavage reaction mixture is in the liquid phase.

In various embodiments in which the acidic material is an cation exchange resins, the pressure may be about 10 psig to 200 psig (70 kPa to 1380 kPa) and the temperature may be about 30° C. to about 100° C., such that most of the cleavage reaction mixture is in the liquid phase.

It will be understood that the contaminants in all or a portion of the cleavage reaction mixture may be contacted with an acidic material as disclosed herein. For example, contaminants in a distilled fraction of the entire cleavage reaction mixture containing an enriched or depleted concentration of phenol and/or cyclohexanone relative to the cleavage reaction mixture may be contacted with an acidic material as described herein. When a stream is described as being "enriched" in a specified species, it is meant that the wt % of the specified species in that stream is enriched relative to the feed stream prior to separation. When a stream is described as being "depleted" in a specified species, it is meant that the wt % of the specified species in that stream is reduced relative to the feed stream prior to separation.

Additionally or alternatively, a filtered fraction of the entire cleavage reaction mixture with reduced amounts of filterable components may be contacted with an acidic material as described herein.

Additionally or alternatively, a fraction of the cleavage reaction mixture has undergone an absorbtion operation, such as a water wash, such that absorbable components are reduced in concentration prior to contact with an acidic material.

Additionally or alternatively, a fraction of the cleavage reaction mixture has undergone an adsorption operation, such as passing over a molecular sieve to remove water (e.g., a 3 A molecular sieve) with one or more adsorbable components are reduced in concentration prior to contact with an acidic material.

The contaminant reactor may be any vessel that allows contacting of the contaminant with an acidic material for a suitable residence time. For example, a contaminant reactor may be an open or substantially open vessel reactor or pipe.

In various embodiments, a process for making phenol and cyclohexanone comprises: (i) cleaving a stream comprising cyclohexyl-1-phenyl-1-hydroperoxide in the presence of an acidic cleavage catalyst to produce a cleavage reaction mixture comprising phenol, cyclohexanone, acidic cleavage catalyst, and one or more contaminants; (ii) reacting at least a portion of the acidic cleavage catalyst with a basic material to form a neutralized stream; (iii) separating the neutralized stream into one or more streams rich in cyclohexanone, phenol and/or cyclohexylbenzene, relative to the neutralized stream; and (iv) contacting one or more of the cyclohexanone-rich portion, the phenol-rich portion, and the cyclohexylbenzene-rich portion with an acidic material to remove one or more contaminants.

In various embodiments, the cleavage reaction mixture is separated into: (1) an overhead product that comprises greater than about 98 wt %, or greater than about 99 wt %, of cyclohexanone, based upon total weight of the overhead product and (2) a bottoms product comprising phenol and cyclohexanone in azeotropic proportion. The impurities contained in the overhead product may include methylcyclopentanone. As used herein, "azeotropic proportion" means about 65 wt %-75 wt % phenol and about 23 wt %-35 wt % cyclohexanone, or about 72 wt % phenol and about 28 wt % cyclohexanone, based upon total weight of the stream. In various embodiments, a portion or the entire cleavage reaction mixture may be combined with another stream from the overall phenol production process. For example, the cleavage reaction mixture may be combined with a stream containing cyclohexanone produced by the hydrogenation of phenol. Additionally or alternatively, the cleavage reaction mixture may be combined with a stream containing phenol that is produced by the dehydrogenation of cyclohexanone. Additionally or alternatively, the cleavage reaction mixture may be combined with one or more additives, such as an antifoam or surfactant agent.

In various embodiments, contaminants in more than one portion of the cleavage reaction mixture may be contacted with an acidic material. For example, the cleavage reaction mixture may be separated into one or more streams rich in cyclohexanone, phenol and/or cyclohexylbenzene, relative to the cleavage reaction mixture and each stream may be contacted with an acidic material. The acidic material may be the same or different for each fraction.

In various embodiments, a given fraction of the cleavage reaction mixture may undergo more than one contacting steps with an acidic material. For example, a cyclohexanone-rich fraction derived from distillation of the entire cleavage reaction mixture may first be contacted with a first acidic material (e.g., sulfuric acid) and then separately exposed to a second acidic material (e.g., a cation exchange resin).

Non-limiting examples to the reactions that can occur in converting the contaminants in the cleavage reaction product to converted contaminants include:
  aldol condensation, especially of ketones and aldehydes;
  dehydration, especially of alcohols;
  alkylation, especially of olefins and alcohols with phenols or alkylatable aromatics;
  oligomerization of olefins;
  combinations of alkylation and cyclization of the alkylation products;
  esterification, especially of carboxylic acids and alcohols;
  cracking, especially of alkyl and aryl moieties;
  where the contaminant byproduct reacts with a phenol molecule;
  where the contaminant byproduct reacts with a cyclohexanone molecule;
  where the contaminant byproduct reacts with another contaminant byproduct of the same or different species; and
  any combination of the above.

In various embodiments, the converted contaminants include:
  a property that makes them more separable from phenol and/or cyclohexanone than the starting contaminant. "Separable" can mean distillable, e.g., the converted contaminant does not form an azeotrope with phenol and/or cyclohexanone, whereas the starting contaminant byproduct does; or filterable, or absorbable (e.g., in water or the aqueous acidic material), or adsorbable;
  a molecular weight higher than the starting contaminant;
  a molecular weight lower than the starting contaminant;
  a volatility lower than the starting contaminant, and conveniently considerably lower than cyclohexanone and/or phenol;
  a volatility higher than the starting contaminant, conveniently considerably higher than cyclohexanone and/or phenol;
  aldol condensation products, generally aldehydes and ketones;
  water, generally from neutralization of bases;
  alcohols, from saponification of esters; and
  acid salts, from a neutralization or saponification reaction.

In various embodiments, at least about 20.0%, or at least about 50.0%, or at least about 80.0%, or at least about 90.0%, or at least about 99.9%, or essentially all of any one contaminant is converted to a converted contaminant, based on weight %.

In various embodiments, at least about 20.0 wt %, or at least about 50.0 wt %, or at least about 80.0 wt %, or at least about 90.0 wt %, or at least about 99.9 wt % of any olefin contaminants, including furans and alcohols, are converted to a converted contaminant, the wt % based upon total weight of the stream.

In various embodiments, at least about 20.0 wt %, or at least about 50.0 wt %, or at least about 80.0 wt %, or at least about 90.0 wt %, or at least about 99.9 wt %, or essentially all of all of the contaminants present in the stream are converted to a converted contaminant, the wt % based upon total weight of the stream.

Processing of Treated Cleavage Reaction Mixture

In various embodiments, after one or more contaminants in the cleavage reaction mixture is contacted with an acidic material, the stream may be separated into one or more streams rich in phenol, cyclohexanone and/or cyclohexylbenzene, relative to the feed stream. These streams may be substantially or completely free of contaminants.

In various exemplary embodiments, the process further comprises separating the contaminant-treated stream into a first stream that is enriched in cyclohexanone or phenol or both and a second stream that is enriched in converted contaminant relative to the contaminant-treated stream.

Heat Treatment

In various embodiments, some or all of the contaminants (e.g., in the cleavage reaction mixture or some portion of the cleavage reaction mixture) are subjected to heat treatment conditions upstream or downstream of the contaminant treatment.

For example, the temperature of all or a portion of the cleavage reaction mixture may be raised to at least about 100° C., or about 150° C. to about 185° C., or at least about 200° C. to produce a heat-treated cleavage reaction mixture. In various embodiments, the temperature may be less than about 250° C., or less than about 225° C. The temperature may be any range of the aforementioned temperatures. In various embodiments, the heat treatment conditions include a residence time may be at least 1 min., 2 min., 3 min., 5 min., 10 min., or 15 min. The residence time may be less than about 120 min., 60 min., or 30 min. The residence time may be any logical range of the aforementioned times.

In one embodiment, during heat treatment at least about 1 wt %, or 10.0 wt %, or 20.0 wt %, or 50.0 wt %, or 80.0 wt %, or 90.0 wt %, or 99.0 wt %, or 99.9 wt % or all of any one contaminant (e.g., hydroxycyclohexanone, or other oxyketones such as hexanophenone, 6-hydroxyhexanophenone, 6-hydroperoxyhexanophenone, benzoic acid, pentanal, pentanone, 2-hydroxycyclohexanone, phenylcyclohexanone, or unreacted peroxides) is converted to a converted contaminant.

In various embodiments, no greater than about 80.0 wt %, or 50.0 wt %, or 30.0 wt %, or 20.0 wt %, or 10.0 wt % of contaminant hydroxycyclohexanone or other oxyketones such as 6-hydroxyhexanophenone, or both are converted to a converted contaminant including a furan with both an olefin and oxygen moiety, such as 1,2,4a,9b-tetrahydrodibenzo[b,d]furan that may result from the dehydration, alkylation, and cyclization reaction of phenol and hydroxycyclohexanone.

In various embodiments, the heat-treated stream may be separated into one or more streams rich in one or more of cyclohexanone, phenol, and/or cyclohexylbenzene, relative to the heat-treated stream. These fractions may comprise little or no converted contaminants.

The heat treatment may be conducted in a simple vessel or pipe, which may be open or have means for mixing, such as baffles or a static mixer for turbulent flow. Further, the heat treatment may take place in a fractionation column, wherein fractionation operating conditions are selected such that the components distilled are exposed to the temperatures and residence times noted at any point or points in the column. The heat treated components may be withdrawn from any point in the fractionation column, as an overhead, bottoms or side composition product. Generally, the heat treatment converts at least some of the contaminants or converted contaminants to other compounds more readily removed from the phenol and/or cyclohexanone.

After contaminant treatment and/or heat treatment or combined contaminant and heat treatment, the converted contaminants will generally have a property that makes them more separable from phenol or cyclohexanone, or both, than the starting contaminant. Separable can be distillable, e.g., the converted contaminant does not form an azeotrope with phenol or cyclohexanone whereas the starting contaminant does, and/or filterable, and/or absorbable. As a result, following contaminant and/or heat treatment, the stream can be subjected to one or more separations ultimately resulting in streams that predominantly comprise cyclohexanone, phenol and converted contaminant.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon 6 and nylon 6,6.

The phenol produced through the processes disclosed herein may be used, for example, to produce phenolic resins, bisphenol A, ε-caprolactam, adipic acid and/or plasticizers.

DESCRIPTION ACCORDING TO THE FIGURES

The invention will now be more particularly described with reference to the accompanying drawings.

Figure 1:
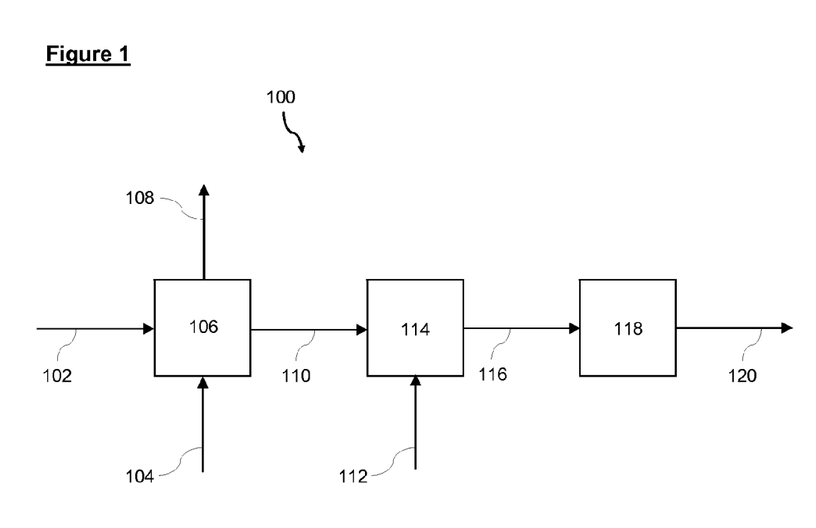
FIG. 1 is a simplified flow diagram of a process according to an embodiment of the invention for producing phenol and cyclohexanone from cyclohexylbenzene.

Referring to FIG. 1, a process 100 for producing phenol and cyclohexanone from cyclohexylbenzene according to a first example of the invention is shown in which a feedstock comprising cyclohexylbenzene is supplied by line 102 to an oxidation reactor 106. A stream comprising oxygen, conveniently air, is also provided to the oxidation reactor 106 in line 104. The stream in line 104 may also be one derived from air, for example, air that has been compressed and filtered to remove particulates, air that has been compressed and cooled to condense and remove water, or a stream that has been enriched in oxygen above the natural approximately 21 mol % in air through membrane enrichment, cryogenic separation or other known means.

Oxidation reactor 106 may be any type of reactor and, for example, comprise a simple, largely open vessel container with a distributor inlet for the oxygen-containing stream in line 104, or otherwise ensure good contacting of the oxygen and cyclohexylbenzene. Oxidation reactor 106 may have means to withdraw and pump a portion of its contents through a suitable cooling device and return the cooled portion to the reactor 106, thereby managing the exothermicity of the oxidation reaction. Alternatively, cooling coils providing indirect cooling, say by cooling water, may be operated within oxidation reactor 106 to remove the generated heat. In other embodiments, oxidation reactor 106 may comprise a plurality of reactors in series, each conducting a portion of the conversion reaction, optionally operating at different conditions selected to enhance the oxidation reaction at the pertinent conversion range in each.

Conditions within oxidation reactor 106 are such that an oxidation reaction takes place, converting cyclohexylbenzene to the associated hydroperoxide. Conveniently conditions are selected to favor the formation of cyclohexyl-1-phenyl-1-hydroperoxide well above other hydroperoxides and dihydroperoxides discussed herein. In one particular embodiment, N-hydroxyphthalimde (NHPI) is also introduced to oxidation reactor 106, by means not shown in FIG. 1, to enhance selectivity to cyclohexyl-1-phenyl-1-hydroperoxide.

As the oxidation reaction proceeds, oxygen is depleted and an oxygen depleted stream in line 108 is removed from oxidation reactor 106. When the stream comprising oxygen in line 104 is air, the oxygen depleted stream in line 108 is typically enriched in nitrogen. When the oxidation reaction is conducted at or near atmospheric pressure, the oxygen depleted stream in line 108 may also contain lower volatility byproducts of the oxidation reaction, such as water, along with minor amounts of cyclohexylbenzene, among other components that may be in the vapor phase under the conditions in oxidation reactor 106. In an operation not shown in FIG. 1, the oxygen depleted stream in line 108 may be further processed to recover the cyclohexylbenzene, remove water, and otherwise make the cyclohexylbenzene fit for recycle as feed to oxidation reactor 106, and make other streams suitable for other uses or disposal.

An oxidation reaction product including cyclohexylbenzene hydroperoxide conveniently rich in cyclohexyl-1-phenyl-1-hydroperoxide but potentially including other hydroperoxides and dihydroperoxides, is withdrawn from oxidation reactor 106 via line 110. Where NHPI is introduced to oxidation reactor 106, the oxidation reaction product removed in line 110 may also contain NHPI.

The oxidation product including cyclohexylbenzene hydroperoxide in line 110 is supplied to a cleavage reactor 114, which also receives a catalyst that will promote the cleavage reaction, such as sulfuric acid, by way of line 112. Conditions in cleavage reactor 114 are such that a cleavage reaction takes place, causing the cyclohexyl-1-phenyl-1-hydroperoxide and any other hydroperoxides and dihydroperoxide present to decompose to phenol, cyclohexanone and contaminant byproducts. A cleavage reaction product including phenol, cyclohexanone, contaminant byproducts and possibly unreacted cleavage catalyst is withdrawn from cleavage reactor 114 in line 116.

Cleavage reactor 114 may be any type of reactor known to those skilled in the art, for example, comprising a simple, largely open vessel container operating in a near continuous stirred tank reactor mode, or a simple, open length of pipe operating in a near plug flow reactor mode. Cleavage reactor 114 may have means to withdraw and pump a portion of the contents through a suitable cooling device and return the cooled portion to cleavage reactor 114, thereby managing the exothermicity of the cleavage reaction, or it may be operated in an adiabatic fashion. In one embodiment, the catalyst promoting the cleavage reaction may be introduced to cleavage reactor 114 in such a circulating portion of the contents, with or without cooling. Alternatively, cooling coils providing indirect cooling, say by cooling water, may be operated within cleavage reactor 114 to remove the generated heat. In other embodiments, cleavage reactor 114 may comprise a plurality of reactors in series, each conducting a portion of the conversion reaction, optionally operating in different modes and at different conditions selected to enhance the cleavage reaction at the pertinent conversion range in each.

The cleavage reaction product in line 116 is directed to an acid material contacting device 118, which contains an acidic material. The conditions within the contacting device 118 are such that a purification reaction takes place, and at least some of the contaminant byproducts in the cleavage reaction product are converted to purification reaction products. An acid treated stream, containing a reduced content of contaminant byproducts relative to the cleavage reaction product, is removed from contacting device 118 in line 120 and may be subject to further processing by means not shown in FIG. 1 to, for example, further purify phenol and cyclohexanone, separate phenol from cyclohexanone, and the like.

The acid material contacting device 118 may be any device suitably correlated to the acid material utilized therein. In the embodiment depicted in FIG. 1, no acid material in a separate line is provided to the contacting device 118. Such an embodiment is representative of, for example, a solid acid material such as, for example, an ion exchange resin or a zeolite. In a variation of such an embodiment, the acidic material is the same acid used as the catalyst for promoting the cleavage reaction, and the acid material contacting device 118 may be a simple, largely open vessel reactor, or largely open pipe allowing continued exposure of the acid and the cleavage reaction product for the desired residence time.

In another embodiment, the acid material may be a liquid aqueous acid and acid material contacting device 118 may be a countercurrent wash column, or a liquid-liquid extraction column or countercurrent series of liquid-liquid contacting drums. In such an embodiment, lines not shown in FIG. 1 may be present carrying the fresh liquid acid material into and the used liquid acid material out of acid material contacting device 118.

In a further embodiment, the cleavage product further contains unreacted cleavage catalyst, and that material is not the desired acid material for facilitating the purification reaction. One option in such a circumstance is to provide means not shown in FIG. 1 to remove the unreacted catalyst from the cleavage product in line 116, or neutralize the material and render it essentially inert, and provide the resultant cleavage product to acid material contacting device 118. In this manner, the desired acid material and acid material contacting device 118 can independently and optimally facilitate the purification reaction on the cleavage product.

Figure 2:
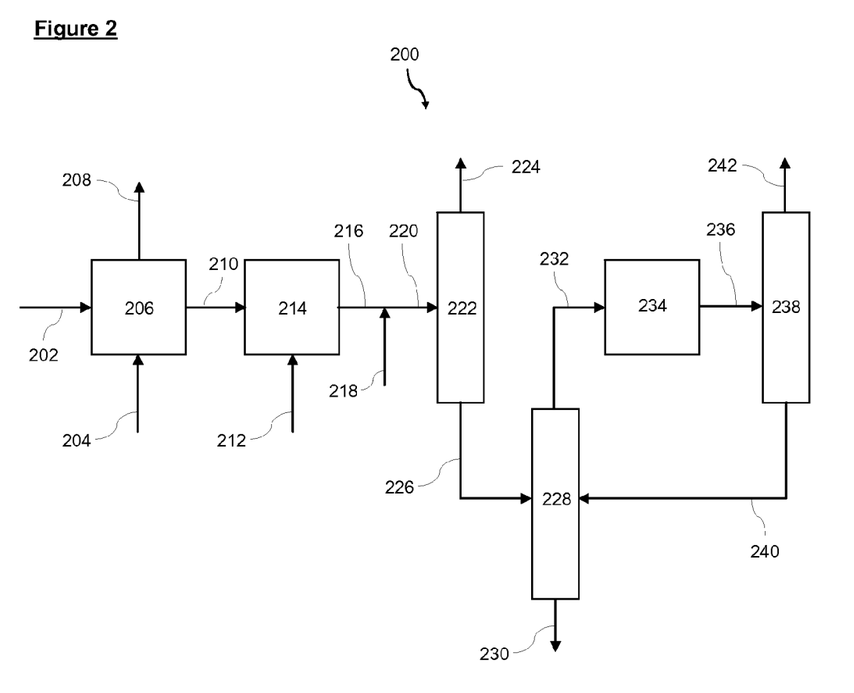
FIG. 2 is a simplified flow diagram of a process according to another embodiment of the invention for producing phenol and cyclohexanone from cyclohexylbenzene.

Referring to FIG. 2, a process 200 for producing phenol and cyclohexanone from cyclohexylbenzene according to a second example of the invention is shown in which a feedstock comprising cyclohexylbenzene is supplied by line 202 to an oxidation reactor 206. A stream comprising oxygen, which can have the same composition as that in line 104 in FIG. 1, is also provided to the oxidation reactor 206 via line 204.

The construction and operation of the oxidation reactor 206 are the same as that of reactor 106 in FIG. 1, including the withdrawal of an oxygen depleted stream in line 208 and an oxidation reaction product including cyclohexylbenzene hydroperoxide in line 210. The oxidation reaction product is supplied by line 210 to a cleavage reactor 214, which also receives sulfuric acid to promote the cleavage reaction by way of line 212.

The construction and operation of the cleavage reactor 214 are the same as that of reactor 114 in FIG. 1, including the withdrawal of a cleavage reaction product including phenol, cyclohexanone, contaminant byproducts and unreacted sulfuric acid from cleavage reactor 214 in line 216. The cleavage reaction product in line 216 is mixed with an amine compound, conveniently a relatively high molecular weight amine, for example, 2-methylpentane-1,5-diamine, in line 218 to complex with and neutralize the sulfuric acid in the cleavage reaction and produce a neutralized cleavage product in line 220. The neutralized cleavage product in line 220 thus now comprises phenol, cyclohexanone, contaminant byproduct(s) and amine-sulfuric acid salt(s). The amine-sulfuric acid salts are completely soluble in the balance of the neutralized cleavage product and further have a relatively low volatility compared to cyclohexylbenzene. In one embodiment, an excess of an amine compound is supplied in line 218 beyond the stoichiometric neutralization of the sulfuric acid in the cleavage product line 216, to give the neutralized cleavage product in line 220 with a more basic, or less acidic character.

The neutralized cleavage product in line 220 is provided to first fractionation column 222, which is operated to provide a first overhead product in line 224 that is rich in material with a higher volatility than cyclohexanone, for example, comprising methylcyclopentanone that may be present in the neutralized cleavage product in line 220, and conveniently further has a very low content of cyclohexanone, phenol, cyclohexylbenzene and lower volatility components. First fractionation column 222 is operated to provide a converse first bottoms product in line 226 that is rich in cyclohexanone and lower volatility components, and further includes contaminant byproducts difficult to fractionate from cyclohexanone and phenol, and conveniently has a very low content of material with a higher volatility than cyclohexanone. Further, the first bottoms product in line 226 is rich in, conveniently containing all of, the amine-sulfuric acid salt(s) introduced to first fractionation column 222 in the neutralized cleavage product in line 220.

The first bottoms product in line 226 is provided to second distillation column 228, which is operated to provide a second overhead product in line 232 that is rich in phenol and cyclohexanone, and further includes contaminant byproducts, and is lean in cyclohexylbenzene and lower volatility components, and lean in recycled purification reaction products. Second distillation column 228 is operated to provide a converse second bottoms product in line 230 that is rich in cyclohexylbenzene and lower volatility components, and rich in recycled purification reaction products, and conveniently is lean in phenol and cyclohexanone. Further, the second bottoms product in line 230 is rich in, conveniently containing all of, the amine-sulfuric acid salt(s) introduced to second fractionation column 228 in the first bottoms product in line 226.

The second overhead product in line 232 is directed to an acid material contacting device 234. Acid material contacting device 234 contains an acidic material, and conditions within acid material contacting device 234 are such that a purification reaction takes place, and some of the contaminant byproducts are converted to a purification reaction product. An acid treated stream, containing a reduced content of contaminant byproducts relative to that provided with the second overhead product in line 232, is removed from acid material contacting device 234 in line 236.

The construction and operation of the acid material contacting device 234 are the same as that of device 118 in FIG. 1, including the withdrawal of an acid treated stream in line 236. The acid treated stream, which contains a reduced content of contaminant byproducts and is enriched in purification product less volatile than phenol and cyclohexanone, is directed by line 236 to a third fractionation column 238, which is operated to provide a third overhead product in line 242 that is rich in phenol and cyclohexanone, and is lean in contaminant byproducts and purification reaction products. Third distillation column 238 is operated to provide a converse third bottoms product in line 240 that is rich in purification reaction products, and conveniently is lean in phenol and cyclohexanone. In one embodiment, the third bottoms product in line 240 contains sufficient phenol, or phenol and cyclohexanone, to carry within it some of the contaminant byproducts that may not have undergone a purification reaction in acid material contacting device 234.

The third bottoms product in line 240 containing purification products and optionally phenol and cyclohexanone is recycled to the second fractionation column 228. In this manner, any phenol and cyclohexanone present in the third bottoms product in line 240 will be recovered in the second overhead product in line 232, and the purification reaction products will removed in the second bottoms product in line 230.

In one embodiment, the operation of first fractionation column 222, or of second fractionation column 228, or both, is conducted in a manner such that the contaminant byproducts within a column(s) are exposed to a temperature for a residence time, that is heat treating conditions, that causes at least a portion of the contaminant byproducts to undergo a second purification reaction, and convert them into a second purification product of lower volatility than cyclohexanone, or of phenol, or of both. Optionally, this second purification reaction by heat treating may be enhanced by an additive, for example, a superstoichiometric addition of an amine with volatility lower than cyclohexylbenzene to the cleavage product, discussed above, which is then introduced to the fractionation column(s). The second purification products would then exit the fractionation columns with the first bottoms product in line 226, or the second bottoms product in line 230, or both.

In one embodiment, the invention relates to:

Paragraph 1: A process for producing phenol comprising:
 (a) oxidizing at least a portion of a feed comprising cyclohexylbenzene to produce an oxidation composition comprising cyclohexyl-1-phenyl-1-hydroperoxide;
 (b) cleaving at least a portion of the oxidation composition to produce a cleavage reaction mixture comprising phenol, cyclohexanone and at least one contaminant; and
 (c) contacting at least a portion of the cleavage reaction mixture with an acidic material to convert at least a portion of the contaminant to a converted contaminant, thereby producing a modified reaction mixture.

Paragraph 2: The process of paragraph 1, wherein the contaminant is one or more of an acyclic aliphatic hexanal, an acyclic aliphatic hexanone, a cyclohexenone, a cyclohexyldione, a hydroxycyclohexanone, benzoic acid, a benzoic ester, a cyclohexenyl cyclohexanone, a methylcyclopentenyl cyclohexanone, 1-phenyl-6-hydroxyhexan-1-one, 1-cyclohexyl-6-hydroxyhexan-1-one and a bicyclic twelve carbon hydroperoxide.

Paragraph 3: The process according to paragraph 1 or 2, wherein the acidic material comprises at least one of a microporous acid material, a cation exchange resin, a Bronsted acid, and sulfurous acid or acid salt.

Paragraph 4: The process according to any one of paragraphs 1-3, wherein the acidic material is a solid acid catalyst.

Paragraph 5: The process according to any one of paragraphs 1-4, wherein the acidic material is a sulfurous acid or sulfurous acid salt.

Paragraph 6: The process according to any one of paragraphs 1-5, wherein the contacting (c) is conducted at a temperature of about 30° C. to about 250° C. and a pressure of about 5 kPa to about 3450 kPa.

Paragraph 7: The process according to any one of paragraphs 1-6, wherein the contacting (c) is conducted at a temperature of about 60° C. to about 160° C. and a pressure of about 170 kPa to about 1380 kPa.

Paragraph 8: The process according to any one of paragraphs 1-7, wherein the contaminant is formed during the oxidizing (a).

Paragraph 9: The process according to any one of paragraphs 1-8, wherein the contaminant is formed during the cleaving (b).

Paragraph 10: The process according to any one of paragraphs 1-9, wherein the cyclohexylbenzene is produced by contacting benzene with hydrogen in the presence of a bifunctional catalyst.

Paragraph 11: The process according to paragraph 10, wherein the bifunctional catalyst is a zeolite of the MCM-22 family containing at least one metal selected from palladium, ruthenium, nickel, zinc, tin and cobalt.

Paragraph 12: The process according to paragraph 10 or 11, wherein the contaminant is formed in the production of the cyclohexylbenzene and is provided with the feed comprising cyclohexylbenzene in (a).

Paragraph 13: The process according to any one of paragraphs 1-12, further comprising: heating at least a portion of the at least one contaminant upstream of the contacting (c) to a temperature of at least 100° C. to produce a heat-treated cleavage reaction mixture comprising the at least one contaminant.

Paragraph 14: The process according to any one of paragraphs 1-13, further comprising: separating at least a portion of the modified reaction mixture into a first stream rich in at least one of cyclohexanone and phenol relative to the modified reaction product, and a second stream rich in the converted contaminant relative to the modified reaction product.

Paragraph 15: The process according to any one of paragraphs 1-14, further comprising:
 separating at least a portion of the cleavage reaction mixture upstream of the contacting (c) to provide a cyclohexanone-rich fraction containing at least a portion of the contaminants and providing the contaminants in the cyclohexanone-rich fraction to the contacting (c).

Paragraph 16: The process according to any one of paragraphs 1-15, further comprising:
 separating at least a portion of the cleavage reaction mixture to provide at least a phenol-rich fraction containing at least a portion of the contaminants, and providing the contaminants in the phenol-rich fraction to the contacting (c).

Paragraph 17: Phenol produced by the process of any one of paragraphs 1-16.

Paragraph 18: Cyclohexanone produced by the process of any one of paragraphs 1-17.

Paragraph 19: At least one of a phenolic resin, bisphenol A, ε-caprolactam, an adipic acid or a plasticizer produced from the phenol of paragraph 17.

Paragraph 20: At least one of adipic acid, a cyclohexanone resin, a cyclohexanone oxime, caprolactam or nylon produced from the cyclohexanone of paragraph 18.

Paragraph 21: In another embodiment, the invention relates to a process for producing phenol comprising:
 (a) introducing oxygen to a feed comprising cyclohexylbenzene to cause an oxidation reaction to occur and produce an oxidation composition comprising cyclohexyl-1-phenyl-1-hydroperoxide;
 (b) introducing an acid catalyst to at least a portion of the oxidation composition to cause a cleavage reaction to occur, and produce a cleavage reaction mixture comprising phenol, cyclohexanone and at least one contaminant; and
 (c) introducing an acidic material to at least a portion of the cleavage reaction mixture to convert at least a portion of the contaminant to a converted contaminant, thereby producing a modified reaction mixture.

Paragraph 22: In another embodiment, the invention relates to a process for producing phenol comprising:
 (a) oxidizing cyclohexylbenzene to produce an oxidation composition comprising cyclohexyl-1-phenyl-1-hydroperoxide;

(b) cleaving at least a portion of the cyclohexyl-1-phenyl-1-hydroperoxide to produce a cleavage reaction mixture comprising phenol, cyclohexanone and at least one contaminant; and (c) contacting at least a portion of the contaminant with an acidic material to convert at least a portion of the contaminant to a converted contaminant, thereby producing a modified reaction mixture.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A mixture comprising:
   (a) 1 wt %-30 wt % phenol;
   (b) 1 wt %-30 wt % cyclohexanone; and
   (c) 0.1 wt %-10 wt % of at least one of water, bicyclohexane, cyclohexenylbenzene, methylcyclopentanone, 1-phenylhexan-1-one, cyclohexyldione, cyclohexanol, cyclohexenone, hydroxycyclohexanone, benzoic acid, phenyl cyclohexanol, hexanal and 1-phenyl-6-hydroxyhexan-1-one,
   wherein the wt % s are based upon the total weight of the mixture.

2. The mixture of claim 1, the mixture further comprising 50 wppm to 3000 wppm of at least one of Bronsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide and sulfur trioxide, wherein the wppms are based upon the total weight of the mixture.

3. The mixture of claim 1, wherein the mixture comprises 5 wt %-15 wt % phenol, based upon the total weight of the mixture.

4. The mixture of claim 1, wherein the mixture comprises 5 wt %-15 wt % cyclohexanone, based upon the total weight of the mixture.

5. The mixture of claim 1, wherein the mixture comprises 5 wt %-15 wt % phenol and 5 wt %-15 wt % cyclohexanone, based upon the total weight of the mixture.

6. The mixture of claim 1, further comprising at least 50 wt % of cyclohexylbenzene, based upon the total weight of the mixture.

7. The mixture of claim 1, wherein the mixture comprises 0.5 wt % to 7 wt % of at least one of water, bicyclohexane, cyclohexenylbenzene, methylcyclopentanone, 1-phenylhexan-1-one, cyclohexyldione, cyclohexanol, cyclohexenone, hydroxycyclohexanone, benzoic acid, phenyl cyclohexanol, hexanal and 1-phenyl-6-hydroxyhexan-1-one, wherein the wt % s are based upon the total weight of the mixture.

8. The mixture of claim 1, wherein the mixture comprises 100 wppm to 3.0 wt % of water, based upon total weight of the mixture.

9. The mixture of claim 1, wherein the mixture comprises 10 wppm to 3.0 wt % of any one of bicyclohexane, cyclohexenylcyclohexane, and cyclohexadienylcyclohexane, cyclohexenylbenzene, cyclohexadienylbenzene, and biphenyl, based upon total weight of the mixture.

10. The mixture of claim 1, wherein the mixture comprises 10 wppm to 1.0 wt % of cyclohexyldione(s), wherein the wppm and wt % are based upon total weight of the mixture.

11. The mixture of claim 1, wherein the mixture comprises 10 wppm to 1.0 wt % of cyclohexene, wherein the wppm and wt % are based upon total weight of the mixture.

12. The mixture of claim 1, wherein the mixture comprises 10 wppm to 1.0 wt % of cyclohexanol, wherein the wppm and wt % are based upon total weight of the mixture.

13. The mixture of claim 1, wherein the mixture comprises 10 wppm to 2.0 wt % of cyclohexenone(s), wherein the wppm and wt % are based upon total weight of the mixture.

14. The mixture of claim 1, wherein the mixture comprises 10 wppm to 2.0 wt % of hydroxycyclohexanone(s), wherein the wppm and wt % are based upon total weight of the mixture.

15. The mixture of claim 1, wherein the mixture comprises 10 wppm to 1.0 wt % of benzoic acid, wherein the wppm and wt % are based upon total weight of the mixture.

16. The mixture of claim 1, wherein the mixture comprises 10 wppm to 5.0 wt % of phenyl cyclohexanol(s), wherein the wppm and wt % are based upon total weight of the mixture.

17. The mixture of claim 1, wherein the mixture comprises 10 wppm to 1.0 wt % of cyclohexyl cyclohexanol(s), wherein the wppm and wt % are based upon total weight of the mixture.

18. The mixture of claim 1, wherein the mixture comprises 10 wppm to 1.0 wt % of unsaturated alkyl oxygenated cyclohexanes, wherein the wppm and wt % are based upon total weight of the mixture.

19. The mixture of claim 1, wherein the mixture comprises 10 wppm to 1.0 wt % of any one of pentanals, hexanals, cyclohexyl or methylcyclopentyl alkyl aldehydes, wherein the wppm and wt % are based upon total weight of the mixture.

20. The mixture of claim 1, wherein the mixture comprises 10 wppm to 4.0 wt % of 1-phenyl-6-hydroxyhexan-1-one, wherein the wppm and wt % are based upon total weight of the mixture.

21. The mixture of claim 1, wherein the mixture comprises 10 wppm to 1.0 wt % of any one of benzoic esters, wherein the wppm and wt % are based upon total weight of the mixture.

22. The mixture of claim 1, wherein the mixture comprises 10 wppm to 1.0 wt % of at least one of cyclohexyl-1-phenyl-1-hydroperoxide, cyclohexyl-1-phenyl-2-hydroperoxide, cyclohexyl-1-phenyl-3-hydroperoxide, cyclohexyl-1-phenyl-4-hydroperoxide; cyclopentyl-1-methyl-2-phenyl-2-hydroperoxide, cyclopentyl-1-methyl-3-phenyl-3-hydroperoxide, cyclopentyl-1-methyl-1-phenyl-2-hydroperoxide, cyclopentyl-1-methyl-1-phenyl-3-hydroperoxide; cyclohexyl-1-phenyl-1,2-dihydroperoxide, cyclohexyl-1-phenyl-1,3-dihydroperoxide, cyclohexyl-1-phenyl-1,4-dihydroperoxide, cyclopentyl-1-methyl-2-phenyl-1,2-dihydroperoxide, cyclopentyl-1-methyl-2-phenyl-2,3-dihydroperoxide, cyclopentyl-1-methyl-2-phenyl-2,4-dihydroperoxide, and cyclopentyl-1-methyl-2-phenyl-2,5-dihydroperoxide, wherein the wppm and wt % are based upon total weight of the mixture.

23. A mixture comprising:
   (a) 1 wt %-30 wt % phenol;
   (b) 1 wt %-30 wt % cyclohexanone; and
   (c) 0.1 wt %-10 wt % of at least one of:
      (1) 100 wppm to 3.0 wt % of water;
      (2) 10 wppm to 3.0 wt % of at least one of bicyclohexane and cyclohexenylbenzene;
      (3) 10 wppm to 4.0 wt % of at least one of methylcyclopentanone and 1-phenylhexan-1-one;
      (4) 10 wppm to 1.0 wt % of cyclohexyldione;
      (5) 10 wppm to 1.0 wt % of cyclohexanol;
      (6) 10 wppm to 2.0 wt % of cyclohexenone;
      (7) 10 wppm to 2.0 wt % of hydroxycyclohexanone;

(8) 10 wppm to 1.0 wt % of benzoic acid;
(9) 10 wppm to 5.0 wt % of phenyl cyclohexanol;
(10) 10 wppm to 1.0 wt % of hexanal; and
(11) 10 wppm to 4.0 wt % of 1-phenyl-6-hydroxyhexan-1-one, wherein the wppms and wt % s are based upon the total weight of the mixture.

* * * * *